(12) United States Patent
Xu et al.

(10) Patent No.: US 9,104,902 B2
(45) Date of Patent: Aug. 11, 2015

(54) INSTRUMENT-BASED IMAGE REGISTRATION FOR FUSING IMAGES WITH TUBULAR STRUCTURES

(75) Inventors: Di Xu, Baltimore, MD (US); Xin Liu, Scarsdale, NY (US); Luis Felipe Gutierrez, Jersey City, NJ (US)

(73) Assignee: Koninklijke Philips N.V., Eindhoven (NL)

( * ) Notice: Subject to any disclaimer, the term of this patent is extended or adjusted under 35 U.S.C. 154(b) by 228 days.

(21) Appl. No.: 13/640,752

(22) PCT Filed: Mar. 29, 2011

(86) PCT No.: PCT/IB2011/051332
§ 371 (c)(1),
(2), (4) Date: Jan. 28, 2013

(87) PCT Pub. No.: WO2011/128797
PCT Pub. Date: Oct. 20, 2011

(65) Prior Publication Data
US 2013/0195338 A1 Aug. 1, 2013

Related U.S. Application Data

(60) Provisional application No. 61/324,319, filed on Apr. 15, 2010.

(51) Int. Cl.
*G06K 9/00* (2006.01)
*A61B 6/12* (2006.01)
*G06T 7/00* (2006.01)
(Continued)

(52) U.S. Cl.
CPC ............... *G06K 9/0014* (2013.01); *A61B 6/12* (2013.01); *A61B 6/466* (2013.01); *A61B 6/5235* (2013.01); *A61B 6/547* (2013.01); *G06T 7/0028* (2013.01); *A61B 6/03* (2013.01); *A61B 6/4441* (2013.01); *G06T 2207/10081* (2013.01); *G06T 2207/10116* (2013.01); *G06T 2207/30061* (2013.01)

(58) Field of Classification Search
None
See application file for complete search history.

(56) References Cited

U.S. PATENT DOCUMENTS

| 6,711,433 B1 * | 3/2004 | Geiger et al. ................. 600/431 |
| 7,903,856 B2 * | 3/2011 | Pfister et al. .................. 382/128 |
| 2001/0027263 A1 * | 10/2001 | Zylka et al. ....................... 600/9 |

(Continued)

FOREIGN PATENT DOCUMENTS

| WO | 2009044321 A2 | 4/2009 |
| WO | 2009081297 A2 | 7/2009 |

OTHER PUBLICATIONS

Jacques Feldmar, Nicholas Ayache, Fabienne Betting. 3D-2D Projective Registration of Free-Form Curves and surfaces. Computer Vision and Image Understanding. vol. 65, No. 3, Mar. 1997, pp. 403-424, Article IV960499, France.

*Primary Examiner* — Tsung-Yin Tsai (57) ABSTRACT

A system and method for registering three-dimensional images with two-dimensional intra-operative images includes segmenting (24) a tubular structured organ in a three-dimensional image of the organ, and projecting (26) the three-dimensional image of the organ into two-dimensional space to provide a projected image. A medical instrument depicted in a two-dimensional image of the medical instrument is segmented (28). A similarity score is computed between the projected image and a shape of the medical instrument depicted in the two-dimensional image to determine a best match. The projected image is registered (30) to the two-dimensional image based on the best match.

22 Claims, 5 Drawing Sheets

(51) Int. Cl.
*A61B 6/03* (2006.01)
*A61B 6/00* (2006.01)

(56) References Cited

U.S. PATENT DOCUMENTS

| | | | |
|---|---|---|---|
| 2003/0181809 A1* | 9/2003 | Hall et al. | 600/425 |
| 2003/0220561 A1* | 11/2003 | Camus et al. | 600/424 |
| 2005/0203420 A1* | 9/2005 | Kleen et al. | 600/476 |
| 2006/0188139 A1 | 8/2006 | Khamene et al. | |
| 2006/0235287 A1 | 10/2006 | Desmedt et al. | |
| 2006/0241413 A1 | 10/2006 | Boese et al. | |
| 2007/0055128 A1 | 3/2007 | Glossop | |
| 2007/0078334 A1* | 4/2007 | Scully et al. | 600/424 |
| 2007/0167714 A1* | 7/2007 | Kiraly et al. | 600/407 |
| 2007/0183569 A1* | 8/2007 | Boese et al. | 378/62 |
| 2008/0147086 A1* | 6/2008 | Pfister et al. | 606/130 |

* cited by examiner

INSTRUMENT-BASED IMAGE REGISTRATION FOR FUSING IMAGES WITH TUBULAR STRUCTURES

This disclosure relates to imaging systems and more particularly to a system and method for image registration of internal objects during a medical procedure.

Bronchoscopy is a real-time image modality for inspecting the internal walls of airways and conducting subsequent diagnostic or therapeutic interventions. During a procedure, X-ray imaging can be used for real-time monitoring of the location of an endoscope. Due to the low image contrast of X-ray images, soft tissue structures such as lesions and airways in the lungs are difficult to see. This hinders the utility of X-ray fluoroscopy as a real-time image guidance tool in assisting bronchoscopic interventions.

One solution is to pre-acquire a three-dimensional (3D) computed, tomography (CT) volume, which clearly depicts many structures not visible in two-dimensional (2D) X-ray images, and then overlay the soft tissue information from the CT onto the X-ray images. The fused visualization can provide intra-operative guidance so that one can precisely localize the lesion and identify its spatial relationship to the scope, but can suffer from registration errors and other issues since features are not easily identified in the X-ray images. Registration methods can be classified as intensity-based methods and feature-based methods in general. Feature-based methods enjoy a computational advantage, but the result is dependent upon the accuracy of image segmentation or segmentation (an image processing procedure that aims at extracting features of interest from a background of the image) and characteristics of the features.

Currently, many 2D-3D registration methods are feature-based in nature, and thus, the results highly rely on the characteristic features inside images. Many registration algorithms have demonstrated their feasibility and robustness in cardiac and neurological interventions; for example, the co-registration of coronary arteries between 3D computed tomography angiography (CTA) volume data and 2D angiography.

In fluoroscopic guidance for pulmonology intervention, angiography is rarely available in 2D X-ray images. There are mere hints of airways or other soft tissues presented in the X-ray images. Therefore, the only visible features contained in both types of images are bony features such as spines and ribs. These features are not sufficient to be used for registration because they exhibit highly duplicative patterns in space.

On the other hand, the intensity-based methods, which are based on all the intensity information, have a comparatively small capture range and slow convergence rate. The computation overhead is known to be intensive and thus real-time data fusion is not always feasible.

In accordance with the present principles, a system and method for registering three-dimensional images with two-dimensional intra-operative images includes segmenting a tubular structured organ in a three-dimensional image of the organ, and projecting the three-dimensional image of the organ into two-dimensional space to provide a projected image. A medical instrument depicted in a two-dimensional image of the medical instrument is segmented. A similarity score is computed between the projected image and a shape of the medical instrument depicted in the two-dimensional image to determine a best match. The projected image is registered to the two-dimensional image based on the best match.

Another method for registering images during a medical procedure includes segmenting a tubular structured organ in a pre-operative three-dimensional image of the organ and projecting the three-dimensional image of the organ into two-dimensional space to provide a projected image. Intra-procedural image data is collected for a position of a medical instrument to obtain a two-dimensional image of the medical instrument relative to a region of interest in the organ. The medical instrument depicted in the two-dimensional image is segmented. A similarity score is computed to determine a best match between the projected image and a shape of the medical instrument depicted in the two-dimensional image. The three-dimensional image is registered to the two-dimensional image based on the best match such that the position of the medical instrument and the region of interest are concurrently visible.

A system for registering images in a medical procedure includes a computer processing unit having memory storage media for storing and executing a program for segmenting a tubular structured organ in a three-dimensional image of the organ and projecting the three-dimensional image into a two-dimensional image. An intra-procedural imaging device is configured to obtain a two-dimensional image of the medical instrument in a region of interest. The program is configured to compute a similarity score between the projected image and a segmented image of a medical instrument depicted in the two-dimensional image of the medical instrument to determine a best match. The projected image is registered to the two-dimensional image based on the best match to be rendered on a display device.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

The present disclosure describes instrument-based image registration systems and methods for fusing images with tubular structures. In fluoroscopic guided bronchoscopy intervention, the only visible features in a pre-operative computer tomography (CT) image and intra-operative X-ray image are bony features such as spines and ribs. As mentioned above, these features are not sufficient to be used for registration because they exhibit highly duplicative patterns in space. A novel instrument-based 2D/3D registration system and method are provided to register segmented organs, such as airways, from CT images with an instrument (e.g., endoscope) displayed in fluoroscopic images.

Embodiments can be implemented, e.g., in a bronchoscopic navigation system where X-ray fluoroscopy is needed for a peripheral lesion tissue biopsy. Other embodiments, also can be implemented for other interventions where a catheter or a probe is inserted into a tubular-like structure so that the trajectory of the instrument can be predicted according the human anatomy and pre-operative CT images. The fusion of the anatomic structure and the real-time image of the instrument make it possible for effective fluoroscopic guidance.

In a particularly useful embodiment, an instrument-based 2D/3D registration method registers segmented airways from CT images with an instrument (endoscope) displayed in fluoroscopic images. The method can be implemented in a bronchoscopic navigation system where X-ray fluoroscopy is needed for a peripheral lesion tissue biopsy. The method may include: (1) obtaining pre-operative (pre-op) 3D CT data of a lung or other organ or structure and an on-line X-ray fluoroscopic image; (2) manual, automatic, or semi-automatic segmentation and recognition of an airway, etc.; (3) use of a Digital Radiological Reconstruction (DRR) or similar method for simulating X-ray fluoroscope images by projecting CT data from 3D space into 2D space. (Similar projection methods may include alternative DRR methods, etc. In one embodiment, pixel averaging may be employed to project a triangle surface mesh of the airway from the 3D volume to a 2D virtual image plane. Because the triangle mesh preserves the structure of airway and reduces a size of the data set, this alternative method may be more robust and provide faster results.) (4) use of an instrument (e.g., endoscope) segmentation method to identify the entire scope from X-ray fluoroscope images; and (5) 2D/3D image registration and optimization based on segmented airways and the endoscope. The fusion of the anatomic structure and the real-time image of the instrument make effective fluoroscopic guidance possible.

It should be understood that the present invention will be described in terms of CT images and X-ray fluoroscope images employed in conjunction with a bronchoscopy; however, the teachings of the present invention are much broader and are applicable to any tracking methodology on or for any procedure. It should also be understood that the present invention will be described in terms of endoscopic procedures; however, the teachings of the present invention are much broader and are applicable to any medical procedures or devices. Embodiments described herein are preferably for locating tissues in the lung or near the lungs, but may be in other locations such as the heart, digestive organs, blood vessels, kidney, etc.

It also should be understood that the present invention will be described in terms of medical instruments; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Figure 1:
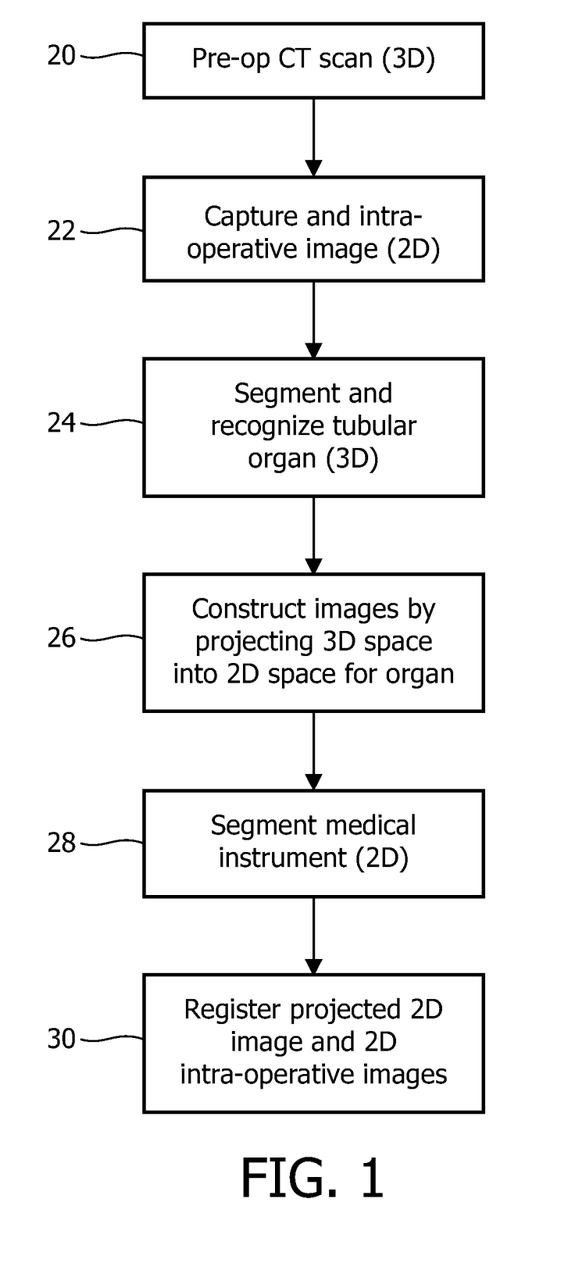
FIG. 1 is a block/flow diagram showing a method for registering images for a medical procedure in accordance with one embodiment.

Referring now to the drawings in which like numerals represent the same or similar elements and initially to FIG. 1, an instrument-based method is provided to register internal organs, such as airways. The internal organs are segmented (e.g., the background of the image is determined and removed) from images (such as CT images) having an endoscope or other device, which is displayed in fluoroscopic images. In block 20, a pre-operative 3D CT scan (3D image) provides data of the lung or other tubular organ. In block 22, an intra-operative image is captured which includes a medical instrument. This may include fluoroscopic images of a region of interest (lesion, etc.) within a body, e.g., an on-line X-ray fluoroscopic image. In block 24, manual, automatic, or semi-automatic segmentation and recognition of the airway or tubular organ are performed in the 3D image.

In block 26, 2D images are constructed by projecting the 3D image into 2D space. Digital Radiological Reconstruction (DRR) or equivalent methods are employed for simulating 2D X-ray fluoroscope images by projecting CT data from 3D space into 2D space. In block 28, an instrument (e.g., endoscope) segmentation method identifies the entire scope from 2D X-ray fluoroscope images. In block 30, image registration and optimization are performed to match the reconstructed 2D images from 3D space having the segmented airways with the 2D segmented endoscope. A shape of the inserted endoscope in the X-ray fluoroscopic images is acquired and is able to be used as a reference for feature-based registration. One assumption is that the endoscope should always be contained within the segments of airways leading toward a targeted lesion. Since segmentation of the endoscope and the internal organ or lesion can be relatively straightforward and reliable, the registration can be performed quite fast. By bringing into coincidence the centerlines or other features extracted from the segmented airways and from the segmented instrument, a real-time data fusion between 3D CT and 2D X-rays can be realized.

Figure 2:
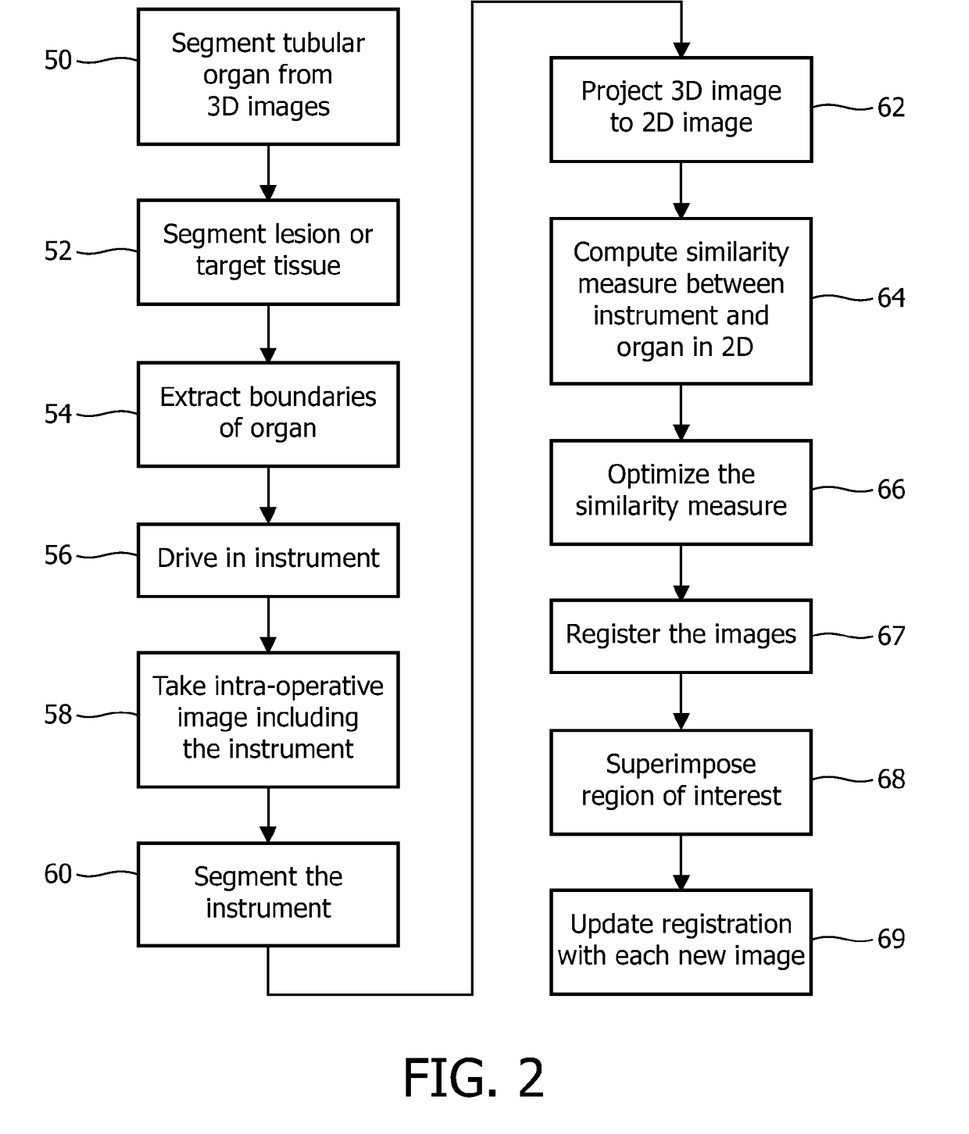
FIG. 2 is a block/flow diagram showing a more detailed method for registering images for a medical procedure in accordance with another embodiment.
Figure 3:
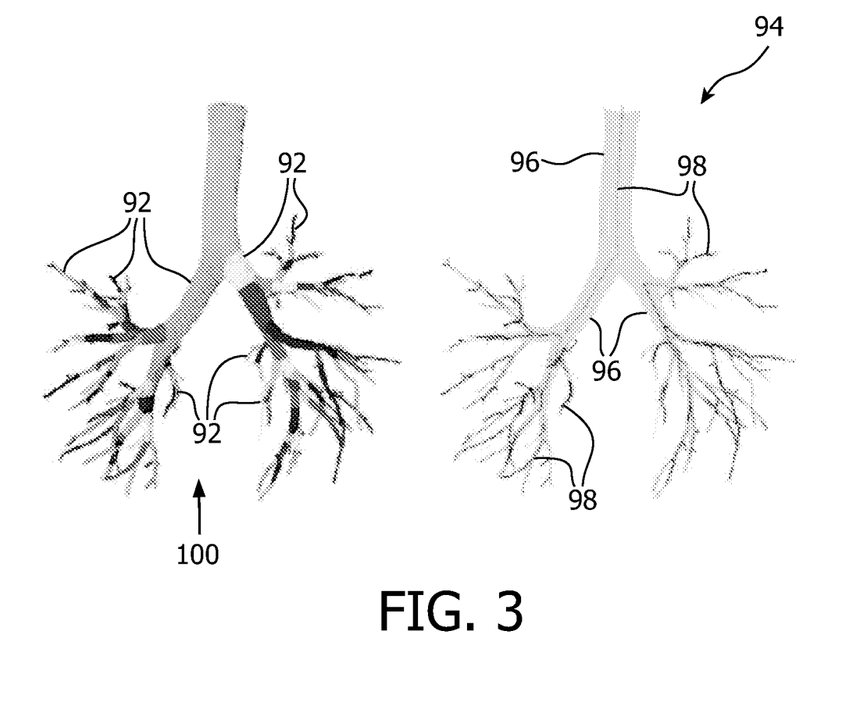
FIG. 3 is an image of segmented bronchial tubes being transformed into a skeleton image with centerlines in accordance with the present principles.

Referring to FIG. 2, a flow diagram shows a more detailed workflow in accordance with the present principles. In block 50, tubular organ(s), such as airways, digestive organs, blood vessels, etc., are segmented from 3D images, e.g., CT scan images, before a procedure (e.g., a bronchoscopy). For example, segmentation can be automated from a trachea to, e.g., the $4^{th}$ generation of airway tubes (peripheral lesions are usually located further than $4^{th}$ generation) or beyond. The process may be manually performed as well. Segmentation of the lesion can be performed, e.g., by semi-automated or manual segmentation, in block 52. The lesion or target tissue may be segmented by various manual or semi-automatic methods. In block 54, a thin skeleton structure or boundaries of the organ (airway) are extracted for further registration steps as depicted in FIG. 3. It may be advantageous to only preserve the airway path leading toward a lesion to conserve memory and reduce complexity. Other segmented airways can be removed.

In block 56, pulmonologists or other medical personnel may drive an instrument (e.g., a scope, such as an, an endoscope or other instrument) to about the $4^{th}$ generation of airways, but may get spatially confused when the scope reaches about $5^{th}$ generation and beyond. A 2D intra-operative image is taken in block 58. This may include an X-ray fluoroscopic image. In a current bronchoscopy procedure, an X-ray fluoroscope technician usually takes the $1^{st}$ shot of X-ray image that has a relatively big field of view (FOV) to capture the endoscope's (bronchoscope's) position. Therefore, the majority of the scope can be seen in a first shot of the X-ray image.

In block 60, the instrument is segmented in the 2D image (e.g., the fluoroscope image) and a skeleton structure of the scope is obtained for further registration purposes. Due to the intra-operative acquisition of X-ray images, manual interaction is not desirable. An automated region growing method, a level set method or other methods can be used to segment the scope. The segmentation of a scope image is preferably from a 2D X-ray image.

In block 62, 3D airways are projected to a virtual 2D detector plane using a DRR method or other suitable method. Note that this reconstruction only needs to be done to pre-operative segmented airways of CT images that lead to the target from the trachea since airway correspondence exists to the trajectory of the instrument. In block 64, a similarity measure is computed between the segmented airway projected to 2D from the CT image space (FIG. 4) and a segmented instrument in a reference X-ray image. The similarity measure may include determining an average distance between feature point sets (e.g., centerlines of the projected airway centerline and depiction of instrument (endoscope) in fluoroscopic images). Alternatively, the similarity measure may also include similarity scores to compare two curves using pre-defined shape descriptors (e.g., compare parameters of curves, e.g., b-spline parameters, etc.). Other features that may be employed include grey scale values, gradients, other image information to compare the images, etc. In block 66, an optimization method may be run to minimize the similarity measure between the segmented airway projected to 2D and the segmented scope. In a couple of iterations, the registration of the $1^{st}$ shot is completed in block 67.

In block 68, the segmented region of interest (e.g., lesion) is superimposed and displayed onto the 2D image (e.g., the X-ray fluoroscope image). This provides a complete image for the navigation of a $1^{st}$ image shot. (See FIG. 6). In block 70, once the $1^{st}$ registration is successful, registration for following X-ray shots is straightforward, given the patient is not moving and the transformation matrix between a C-arm (for an X-ray machine) current pose and a previous pose is known by the mechanics of the C-arm system. Therefore, the complete presence of the scope shape is not necessary for the shots that follow. By implementing instrument-based registration, real-time lesion visualization is feasible. This greatly aids X-ray guided bronchoscopy procedures since bronchoscopists are able to visualize both the instrument and the lesion concurrently.

Referring to FIG. 3, an illustrative image 90 shows bronchi 92 segmented in accordance with a segmentation process. Segmentation is an image-processing term that is used to describe a process to differentiate a structure of interest from the background of the image. Image 90 is processed to thin out the image to leave a thin skeleton structure 94 where boundaries 96 of the bronchi 92 are visible and centerlines 98 are computed. The structure 94 will be projected into 2D for comparison to a segmented image of the instrument for instrument-based registration.

Figure 4:
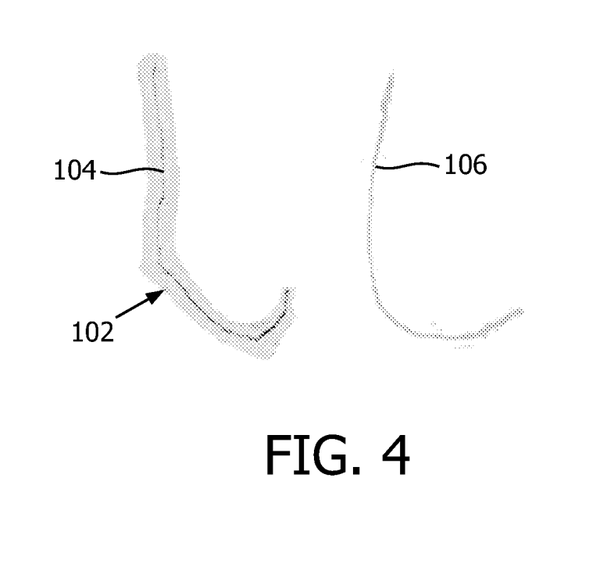
FIG. 4 shows a three-dimensional image of a bronchial tube being projected into two dimensions in accordance with the present principles.

Referring to FIG. 4, a reconstruction of a segmented airway 102 (a bronchus) is illustratively shown. Bronchus 102 is selected from a trachea to a targeted lesion (not shown). A center line 104 of the segmented airway 102 from a 3D CT scan image is projected to an image 106. The bronchus 102 is projected from 3D to 2D using, e.g., DRR to generate a 2D center line image 106. Image 106 will be employed to line up with an image of a medical instrument (110).

Figure 5:
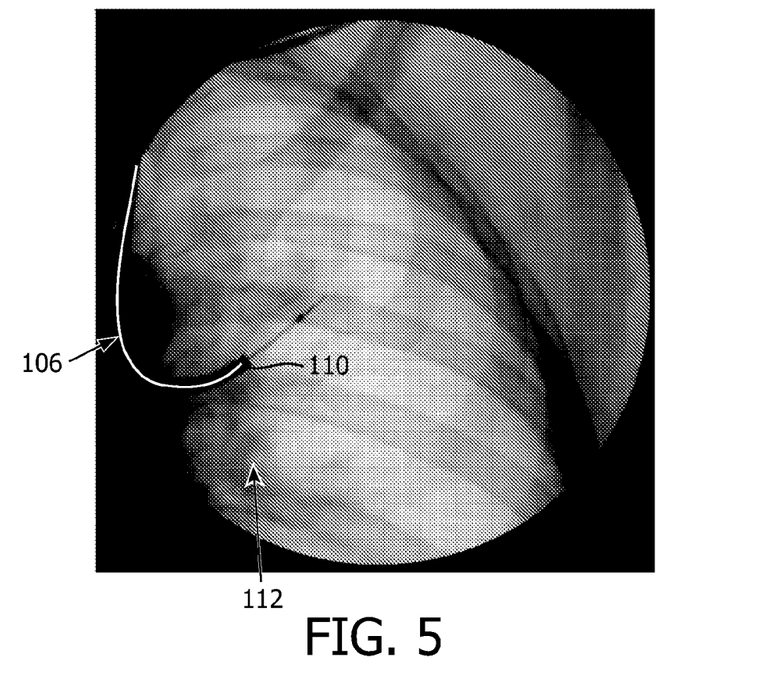
FIG. 5 shows an image of an inserted instrument being registered to a centerline of a projected image of FIG. 4 in accordance with the present principles.
Figure 6:
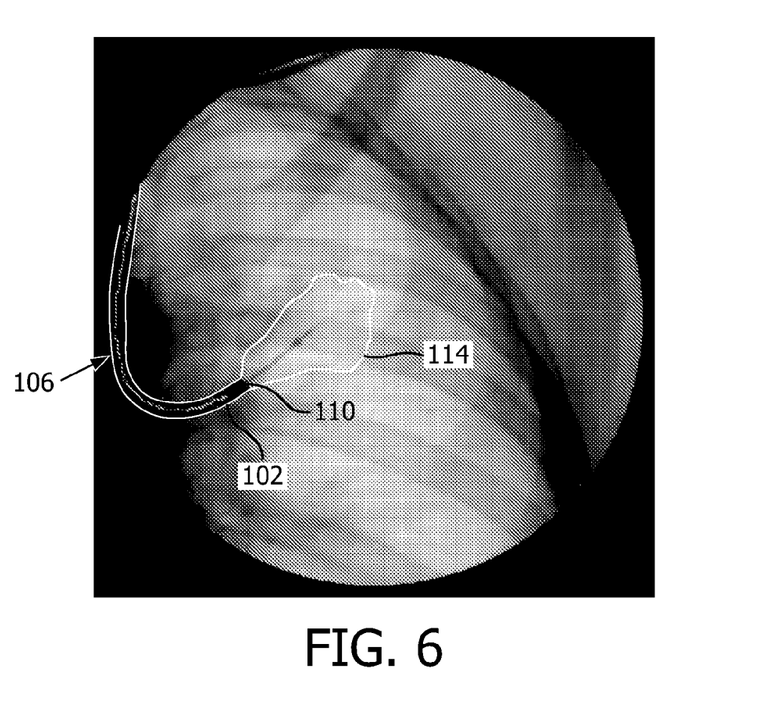
FIG. 6 shows a registration result along with a lesion depicted in a same image in accordance with the present principles.

Referring to FIG. 5, the centerline image 106 from the segmented airway 102 is aligned with an endoscope 110 on an X-ray fluoroscope image 112. FIG. 6 shows a registration result. The X-ray fluoroscope image 112 displays an overlaid lesion 114 and the segmented airway centerline 106 from pre-op CT images. The fused visualization provides intra-operative guidance so that the lesion can be precisely localized and its spatial relationship to the scope identified.

This method can be implemented into a bronchoscopic navigation system where X-ray fluoroscopy is needed for a peripheral lesion tissue biopsy. It also can be implemented for other interventions where a catheter or a probe is inserted into a tubular-like structures so that the trajectory of the instrument can be predicted according the human anatomy and pre-op CT images. The fusion of the anatomic structure and the real-time image of the instrument make it possible for the effective fluoroscopic guidance.

Figure 7:
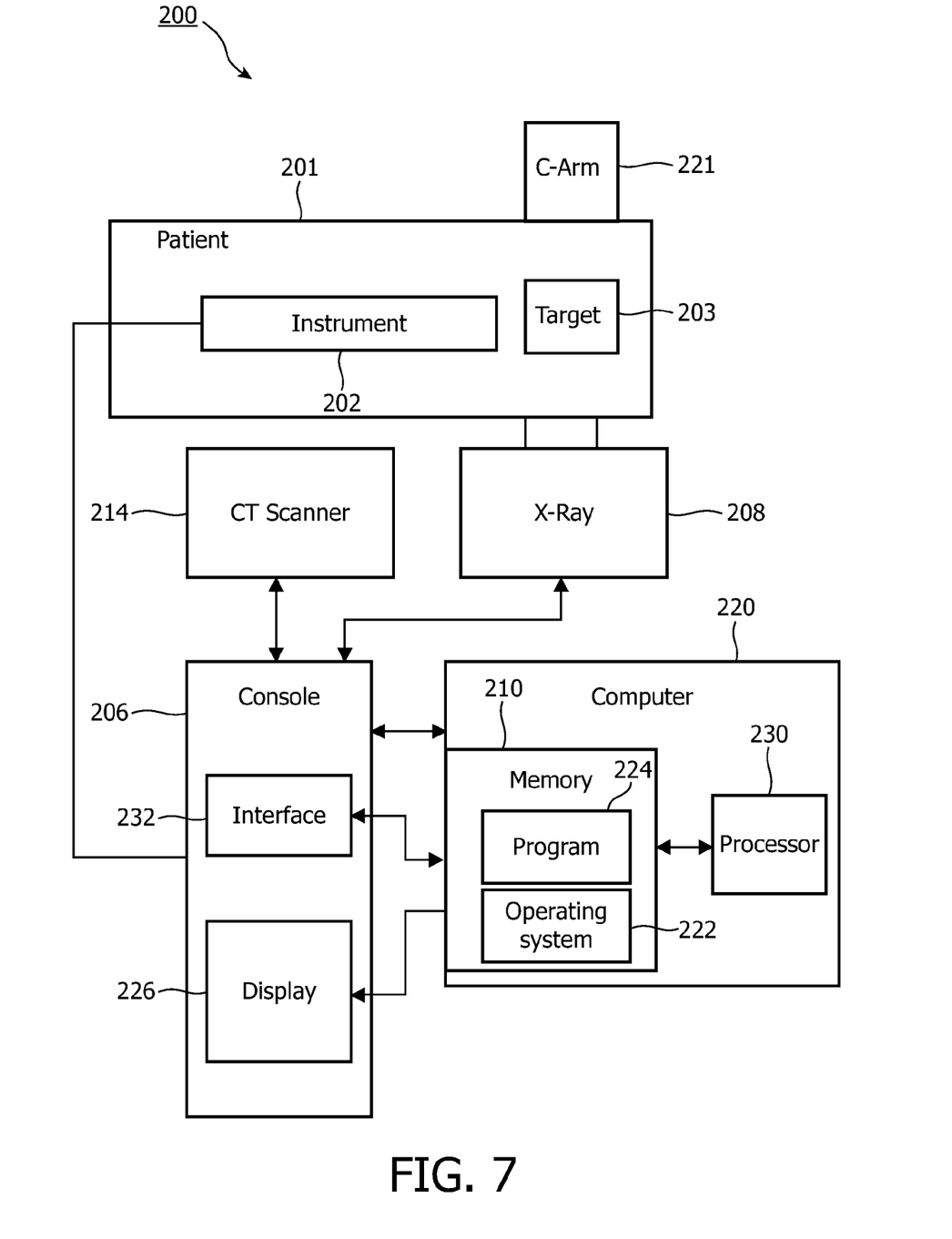
FIG. 7 is a block diagram showing an illustrative system for carrying out a procedure in accordance with the present principles.

Referring to FIG. 7, a system 200 for registering 2D and 3D images during a medical procedure is illustratively shown. System 200 works with a guided medical device, instrument or tool 202, such as an endoscope, catheter, forceps, needle or the like. The instrument 202 is visible in X-ray images. System 200 includes one or more computer consoles 206 employed for collecting/displaying images, registering images, etc. The console or consoles 206 also provide control and support for the medical device(s) 202 during the procedure.

In one embodiment, an X-ray machine 208 is employed to provide radiation for exposure of a patient to develop 2D images. A preferred method for X-raying includes employing a C-arm structure 211, although other arrangements may be employed. Other medical instruments or devices may be provided on the instrument 202 (or independently) for performing a procedure, e.g., lights, forceps, needles, balloons, etc. CT or other images are preferably taken in advance (pre-op) and stored in memory 210. Alternately, a CT scanner 214 may be employed contemporaneously to take CT images in advance of the procedure. Pre-operative 3D CT images stored in memory 210 may include a target region(s) 203 (e.g., suspicious cancer tissue) in a patient 201 which is/are preferably delineated in the CT images.

Console 206 may be connected to or be part of a computer system 220 which includes memory 210 and an operating system 222. Memory 210 may store one or more corresponding program(s) 224 which may provide segmentation, centerline determination, DRR methods and optimization functions to provide the functionality as described in accordance with the present principles (e.g., FIGS. 1 and 2). Program 224 segments the tubular tissues (e.g., airways) from the CT images and segments the instrument 202 in the 2D or X-ray image of the scope and determines a similarity score between the computed centerlines or other features between the images. The program 224 is also configured to register the X-ray with the projected CT images. Program 224 may also be adapted to perform statistical analyses or interpolations on the registration data to predict motion or provide a confidence score on the registration match.

The computer 220 may be one of a plurality of computers or be employed as a single computer. Computer 220 includes a processor 230 that implements the program 224 and provides a plurality of program options and applications. For example, program 224 may include software modules for image rendering, segmentation, centerline visualization, etc.

Computer 220 may provide support or control for other devices in the system. For example, computer 220 may be employed to control exposure settings for the X-ray, movement of the C-arm 211, synchronization of procedure steps (e.g., endoscopic ablation, balloon inflation, etc. statistics or other computations, etc.). An input/output (I/O) device or interface 232 provides for real-time interaction with the computer 220, the instrument (endoscope) 202 and a visual display 226 to compare and show images. Computer system 220 may include the user interface 232 for interacting with the console 206 and/or the instrument 202. The interface 232 may include a keyboard, a mouse, a touch screen system, etc.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for systems and methods instrument-based image registration for fusing images with tubular structures (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A method for registering three-dimensional images with two-dimensional intra-operative images, comprising acts of:
   segmenting a tubular structured organ in a three-dimensional image of the organ;
   projecting the three-dimensional image of the organ into two-dimensional space to provide a projected image;
   segmenting a medical instrument depicted in a two-dimensional image of the medical instrument; and
   registering the projected image of the organ to the two-dimensional image of the medical instrument based on a best match between the projected image of the organ and a shape of the medical instrument depicted in the two-dimensional image.

2. The method as recited in claim 1, wherein the act of segmenting the tubular structured organ includes an act of determining a centerline of the tubular structured organ.

3. The method as recited in claim 2, further comprising an act of computing a similarity score to determine the best match, wherein the act of computing the similarity score includes an act of comparing a centerline of a segmented medical instrument with the centerline of the tubular structured organ to determine the similarity score.

4. The method as recited in claim 1, wherein the tubular structured organ includes airways of a lung and the medical instrument includes a bronchoscope.

5. The method as recited in claim 1, wherein the three-dimensional image includes a pre-operative computer tomography image.

6. The method as recited in claim 1, wherein the two-dimensional image includes an intra-procedure X-ray image.

7. The method as recited in claim 6, wherein the shape of the medical instrument is visible in the two-dimensional image.

8. The method as recited in claim 1, wherein the projecting act includes employing a Digital Radiological Reconstruction (DRR) method to project three-dimensional space into the two-dimensional space.

9. The method of claim 1, further comprising acts of:
   collecting intra-procedural image data for a position of the medical instrument to obtain the two-dimensional image of the medical instrument relative to a region of interest in the organ; and
   computing a similarity score to determine the best match between the projected image and the shape of the medical instrument depicted in the two-dimensional image,
   wherein the registering act registers the three-dimensional image to the two-dimensional image to form a registered image based on the best match such that the position of the medical instrument and the region of interest are concurrently visible in the registered image.

10. A system for registering images in a medical procedure, comprising:
   a computer processing unit having non-transitory computer readable medium for storing and executing a program for segmenting a tubular structured organ in a three-dimensional image of the organ and projecting the three-dimensional image into a two-dimensional image; and
   an intra-procedural imaging device configured to obtain a two-dimensional image of a medical instrument in a region of interest;
   the program being configured to compute a similarity score between the projected image and a segmented image of the medical instrument depicted in the two-dimensional image of the medical instrument to determine a best match, and register the projected image to the two-dimensional image based on the best match to be rendered on a display device.

11. The system as recited in claim 10, wherein the program when executed on the computer processing unit further determines a centerline of the tubular structured organ and determines a centerline for the medical instrument, and compares the centerline of the tubular structured organ and the medical instrument to determine the similarity score.

12. The system as recited in claim 10, wherein the tubular structured organ includes a lung and the medical instrument includes a bronchoscope.

13. The system as recited in claim 10, wherein the three-dimensional image includes a pre-operative computer tomography image.

14. The system as recited in claim 10, wherein the intra-procedural imaging device includes an X-ray machine and the two-dimensional image includes an intra-procedure X-ray image.

15. The system as recited in claim 10, wherein the program includes a Digital Radiological Reconstruction (DRR) method to project three-dimensional space into two-dimensional space.

16. A system for registering three-dimensional images with two-dimensional intra-operative images, the system comprising a processor configured to perform acts of:
   segmenting a tubular structured organ in a three-dimensional image of the organ;
   projecting the three-dimensional image of the organ into two-dimensional space to provide a projected image;
   segmenting a medical instrument depicted in a two-dimensional image of the medical instrument; and
   registering the projected image to the two-dimensional image based on a best match between the projected image of the organ and a shape of the medical instrument depicted in the two-dimensional image.

17. The system of claim 16, wherein the act of segmenting the tubular structured organ includes an act of determining a centerline of the tubular structured organ.

18. The system of claim 17, wherein the processor is further configured to perform an act of computing a similarity score to determine the best match, wherein the act of computing the similarity score includes an act of comparing a centerline of a segmented medical instrument with the centerline of the tubular structured organ to determine the similarity score.

19. The system of claim 16, wherein the tubular structured organ includes airways of a lung and the medical instrument includes a bronchoscope.

20. The system of claim 16, wherein the three-dimensional image includes a pre-operative computer tomography image.

21. The system of claim 16, wherein the shape of the medical instrument is visible in the two-dimensional image, and wherein the two-dimensional image includes an intra-procedure X-ray image.

22. The system of claim 16, wherein the projecting act includes employing a Digital Radiological Reconstruction (DRR) method to project three-dimensional space into the two-dimensional space.

* * * * *